US012270870B2

(12) United States Patent
Akita et al.

(10) Patent No.: US 12,270,870 B2
(45) Date of Patent: Apr. 8, 2025

(54) MAGNETIC SENSOR AND BIOMAGNETIC MEASUREMENT DEVICE

(71) Applicants: NATIONAL INSTITUTE OF ADVANCED INDUSTRIAL SCIENCE AND TECHNOLOGY, Tokyo (JP); AICHI STEEL CORPORATION, Aichi (JP)

(72) Inventors: Ippei Akita, Ibaraki (JP); Michiharu Yamamoto, Aichi (JP); Hitoshi Aoyama, Aichi (JP); Takeshi Kawano, Aichi (JP)

(73) Assignees: NATIONAL INSTITUTE OF ADVANCED INDUSTRIAL SCIENCE AND TECHNOLOGY (JP); AICHI STEEL CORPORATION (JP)

( * ) Notice: Subject to any disclaimer, the term of this patent is extended or adjusted under 35 U.S.C. 154(b) by 112 days.

(21) Appl. No.: 18/258,116

(22) PCT Filed: Dec. 21, 2021

(86) PCT No.: PCT/JP2021/047409
§ 371 (c)(1),
(2) Date: Jun. 16, 2023

(87) PCT Pub. No.: WO2022/138667
PCT Pub. Date: Jun. 30, 2022

(65) Prior Publication Data
US 2024/0019506 A1 Jan. 18, 2024

(30) Foreign Application Priority Data
Dec. 23, 2020 (JP) .................................. 2020-214191

(51) Int. Cl.
*G01R 33/09* (2006.01)
*G01R 33/00* (2006.01)
(Continued)

(52) U.S. Cl.
CPC ....... *G01R 33/091* (2013.01); *G01R 33/0017* (2013.01); *G01R 33/063* (2013.01); *A61B 5/05* (2013.01)

(58) Field of Classification Search
CPC .................. G01R 33/091; G01R 33/0017; G01R 33/063; G01R 33/0094; G01R 33/0041; G01R 33/007; A61B 5/05; A61B 5/0522
See application file for complete search history.

(56) References Cited

U.S. PATENT DOCUMENTS

| | | | |
|---|---|---|---|
| 5,757,184 A * | 5/1998 | Kurihara | G01R 33/02 324/258 |
| 2014/0018792 A1* | 1/2014 | Gang | A61B 18/1492 606/41 |

(Continued)

FOREIGN PATENT DOCUMENTS

| | | |
|---|---|---|
| EP | 2725375 A1 | 4/2014 |
| EP | 3494879 A1 | 6/2019 |

(Continued)

OTHER PUBLICATIONS

International Search Report mailed Feb. 8, 2022 in corresponding PCT International Application No. PCT/JP2021/047409.

*Primary Examiner* — Alvaro E Fortich
(74) *Attorney, Agent, or Firm* — OSTROLENK FABER LLP (57) ABSTRACT

A magnetic sensor includes a magneto-sensitive body whose electromagnetic properties change under an action of an external magnetic field, a coil disposed to obtain an induced voltage proportional to the external magnetic field, a sampler configured to sample the induced voltage generated in the coil and obtains a sampling voltage, and an automatic correction circuit configured to relatively adjust a rise timing of a magneto-sensitive body clock for driving the magneto-sensitive body and a rise timing of a sampler clock for driving the sampler according to the sampling voltage.

7 Claims, 6 Drawing Sheets

(51) Int. Cl.
*G01R 33/06* (2006.01)
*A61B 5/05* (2021.01)

(56) References Cited

U.S. PATENT DOCUMENTS

| | | | |
|---|---|---|---|
| 2015/0212164 A1 | 7/2015 | Lu | |
| 2015/0374250 A1* | 12/2015 | Hatano | ................ A61B 5/0071 600/409 |
| 2018/0335441 A1* | 11/2018 | Hammerschmidt | .... G01P 3/488 |
| 2020/0166587 A1* | 5/2020 | Uemura | ................ H10N 52/80 |

FOREIGN PATENT DOCUMENTS

| | | |
|---|---|---|
| JP | 2000-338207 A | 12/2000 |
| JP | 2003-329745 A | 11/2003 |
| JP | 3645116 B | 5/2005 |
| JP | 2005-283271 A | 10/2005 |
| JP | 3801194 B | 7/2006 |
| JP | 2006-343300 A | 12/2006 |
| JP | 4655247 B | 3/2011 |
| JP | 5924503 B | 5/2016 |
| JP | 6506466 B | 4/2019 |
| WO | WO 2012/176451 A1 | 12/2012 |

\* cited by examiner

MAGNETIC SENSOR AND BIOMAGNETIC MEASUREMENT DEVICE

CROSS-REFERENCE TO RELATED APPLICATIONS

The present application is a 35 U.S.C. §§ 371 national stage application of International Application No. PCT/JP2021/047409 filed Dec. 21, 2021, which claims priority to Japanese Patent Application No. 2020-214191, filed Dec. 23, 2020, the contents of which are incorporated herein by reference.

TECHNICAL FIELD

The present invention relates to a magnetic sensor and a biomagnetic measurement device.

BACKGROUND ART

A magnetic sensor using a magneto-impedance element requires envelope detection for external magnetic field strength detection. Since external magnetic field strength detection has to be performed at high speed, synchronous detection by peak sampling is generally used.

For example, Patent Document 1 discloses a magneto-impedance effect micro magnetic sensor including: a high permeability magnetic head that is excited in a circumferential direction by a pulsed energizing current; a coil wound in the circumferential direction of the high permeability magnetic head; and an electronic switch that detects a first pulse of an induced voltage in the coil.

Patent Document 2 discloses a magnetic sensor including: a magneto-sensitive body whose electromagnetic properties change under the action of an external magnetic field; a drive circuit that supplies an energizing current to the magneto-sensitive body; a detection coil wound around the magneto-sensitive body; and a sample-and-hold circuit that measures an induced voltage value, which is the magnitude of the voltage induced in the detection coil. The sample-and-hold circuit of Patent Document 2 is configured to measure the induced voltage value in synchronization with the interruption of the energizing current by the drive circuit.

Patent Document 3 discloses a magneto-impedance sensor including: a magneto-impedance element that includes a magneto-sensitive wire formed of an amorphous soft magnetic alloy having zero magnetostriction and a detection coil provided around the magneto-sensitive wire with an electric insulator disposed therebetween, and that detects a voltage generated by the detection coil in response to an external magnetic field upon application of a high frequency current to the magneto-sensitive wire; a current supply device that supplies the high frequency current to the magneto-impedance element; and a signal processing circuit that processes an output signal from the detection coil.

Patent Document 4 discloses an ultra-sensitive micro magnetic sensor including: a magnetic field detection element in which a conductive magnetic wire for detecting a magnetic field, a coil wound around it, two electrodes for energizing a magnetic wire, and two electrodes for detecting a coil voltage are placed on a substrate; means for applying a pulse current to the magnetic wire; a signal processing circuit for detecting a coil voltage generated when the pulse current is applied; and means for converting the coil voltage into an external magnetic field H.

Patent Document 5 discloses a magneto-impedance sensor including a magneto-impedance element that applies a pulse current or high frequency current to an amorphous wire and outputs an AC damped oscillating voltage having a magnitude corresponding to an external magnetic field induced in a detection coil wound around the amorphous wire.

CITATION LIST

Patent Documents

[Patent Document 1]
  Japanese Patent No. 3645116
[Patent Document 2]
  Japanese Patent No. 3801194
[Patent Document 3]
  Japanese Patent No. 4655247
[Patent Document 4]
  Japanese Patent No. 6506466
[Patent Document 5]
  Japanese Patent No. 5924503

SUMMARY OF INVENTION

Technical Problem

However, in the magnetic sensors described in Patent Documents 1 to 4, the time from driving the magneto-impedance element to performing peak sampling is adjusted by a delay circuit according to element constant adjustment using a CMOS inverter, an RC circuit, or the like. For this reason, there is a problem that the peak sampling timing shifts due to environmental changes and manufacturing variations, resulting in variations in sensitivity (V/T) of the magnetic sensor.

By applying strong negative feedback (magnetic feedback) with a large loop gain as in Patent Documents 1 and 5, there is a likelihood that variations in the sensitivity (V/T) of the magnetic sensor can be suppressed.

On the other hand, decreased sensitivity due to peak sampling timing errors also reduces the loop gain, resulting in gain fluctuations and noise characteristic deterioration. Thus, appropriate timing adjustment is also required when applying strong negative feedback. However, when the delay amount is individually adjusted (trimmed) by RC time constant or the like for each manufactured magnetic sensor, there is a likelihood of causing a dramatic increase in cost. In addition, as in Patent Documents 1 and 5, even when strong negative feedback is applied, it is not possible to sufficiently suppress sensitivity fluctuations due to environmental changes over time.

The present invention has been made to solve the above problems, and an object of the present invention is to provide a magnetic sensor and a biomagnetic measurement device capable of automatically correcting an optimum sampling timing for synchronous detection without increasing the cost even when there are environmental changes or manufacturing variations and having excellent detection accuracy.

Solution to Problem

In order to solve the above problems, the present invention provides the following means.

(1) According to an aspect of the present invention, there is provided a magnetic sensor including:
a magneto-sensitive body whose electromagnetic properties change under an action of an external magnetic field;
a coil disposed to obtain an induced voltage proportional to the external magnetic field;
a sampler configured to sample the induced voltage generated in the coil and obtain a sampling voltage; and
an automatic correction circuit configured to relatively adjust a rise timing of a magneto-sensitive body clock for driving the magneto-sensitive body and a rise timing of a sampler clock for driving the sampler according to the sampling voltage, in which the automatic correction circuit detects a delay time until the sampling voltage reaches its first peak by observing displacement of the sampling voltage for a predetermined period after the magneto-sensitive body clock rises, and sets the rise timings of the magneto-sensitive body clock and the sampler clock by shifting the rise timings back and forth by a time corresponding to the delay time.
(2) The magnetic sensor according to (1), in which the automatic correction circuit includes
a delay synchronization circuit having a plurality of cascaded delay elements,
a logic circuit that outputs a selection signal Dctrl that selects any one from among outputs of the plurality of delay elements in the delay synchronization circuit each time the sampling voltage is input, and records the selection signal Dctrl output at a timing at which the induced voltage generated in the coil reaches a peak,
a multiplexer that selects any one of the outputs of the plurality of delay elements in the delay synchronization circuit according to the selection signal Dctrl to generate the sampler clock, and
a clock generation circuit that generates the magneto-sensitive body clock.
(3) The magnetic sensor according to (1) or (2), in which the automatic correction circuit further includes a detection circuit configured to output peak sampling state information having information on a timing at which the induced voltage generated in the coil reaches a peak, according to the sampling voltage.
(4) The magnetic sensor according to (3), in which
the detection circuit includes an analog-to-digital conversion circuit, and
the analog-to-digital conversion circuit converts the sampling voltage into the peak sampling state information.
(5) The magnetic sensor according to (3), in which
the detection circuit includes a comparator, and
the comparator outputs information binarized according to a predetermined threshold value as the peak sampling state information.
(6) The magnetic sensor according to any one of (1) to (5), in which a constant current source circuit is connected to the coil.
(7) According to another aspect of the present invention, there is provided a biomagnetic measurement device including:
the magnetic sensor according to any one of (1) to (6); and
a biomagnetic measurement unit configured to measure magnetism emitted by a living body using an output signal from the magnetic sensor.

Advantageous Effects of Invention

According to the present invention, it is possible to provide a magnetic sensor and a biomagnetic measurement device capable of automatically correcting an optimum sampling timing for synchronous detection without increasing the cost even when there are environmental changes or manufacturing variations and having excellent detection accuracy.

DESCRIPTION OF EMBODIMENTS

"Magnetic Sensor"

First Embodiment

First, a magnetic sensor 10 according to a first embodiment of the present invention will be described with reference to the drawings. In the case of the same configuration, the same reference numerals may be attached and a description thereof may be omitted.

Figure 1:
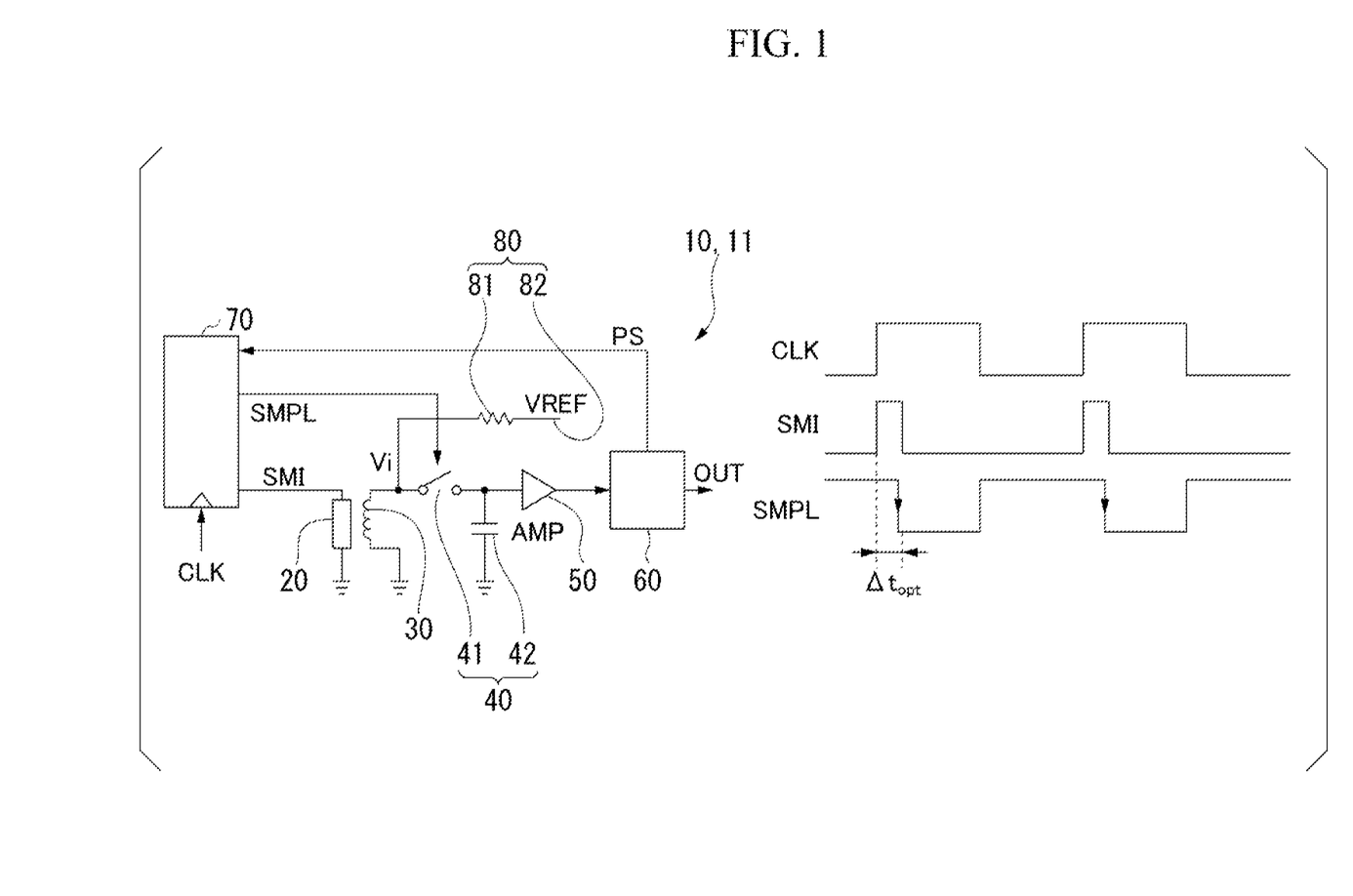
FIG. 1 is a schematic diagram of a magnetic sensor according to a first embodiment of the present invention and a diagram showing an operation example during automatic correction.

As shown in FIG. 1, the magnetic sensor 10 according to the first embodiment of the present invention includes a magneto-sensitive body 20, a coil 30, a sampler 40, an amplifier circuit 50 (AMP), a detection circuit 60, an automatic correction circuit 70, and a constant current source circuit 80.

The coil 30 is disposed to obtain an induced voltage Vi in proportion to an external magnetic field. The sampler 40 is connected to the coil 30 for peak sampling the induced voltage Vi. The sampler 40 is connected to the detection circuit 60 via the amplifier circuit 50. The detection circuit 60 outputs an output signal OUT for displaying a sensing result of the magnetic sensor 10 and peak sampling state information PS having information on a timing at which the induced voltage Vi generated in the coil 30 reaches its peak. The peak sampling state information PS and an external clock CLK are input to the automatic correction circuit 70. The automatic correction circuit 70 generates a magneto-sensitive body clock SMI for driving the magneto-sensitive body 20 in synchronization with the external clock CLK, and a sampler clock SMPL for driving the sampler 40 in synchronization with the external clock CLK.

(Automatic Correction Circuit)

Figure 2:
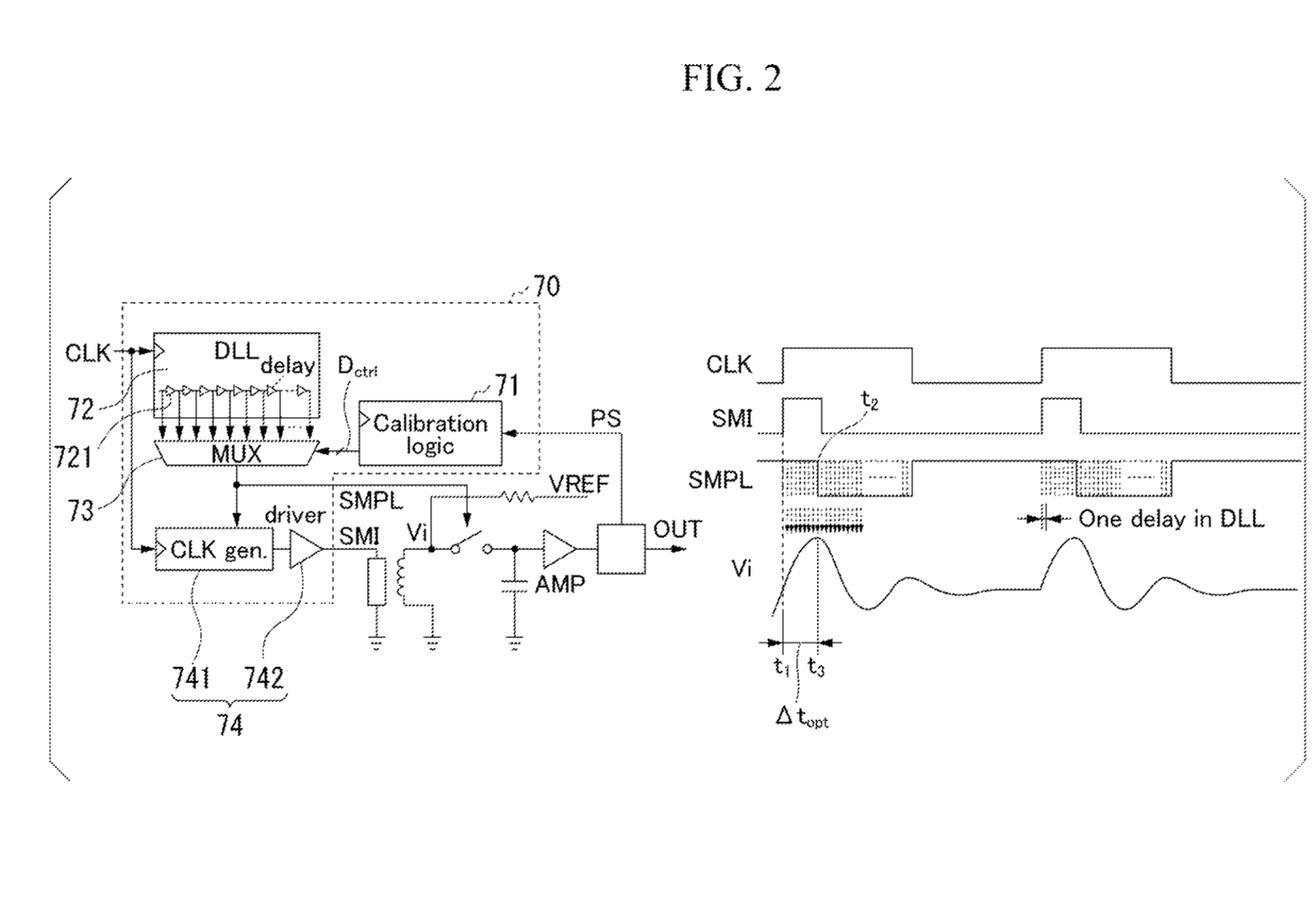
FIG. 2 is a diagram showing details of an automatic correction circuit of the magnetic sensor of FIG. 1 and an operation example during automatic correction.

As shown in FIG. 2, in the magnetic sensor 10 according to the first embodiment of the present invention, the automatic correction circuit 70 includes a logic circuit 71, a delay synchronization circuit 72 (DLL), a multiplexer 73, and a clock generation circuit 74.

According to a sampling voltage detected by the sampler 40, the automatic correction circuit 70 relatively adjusts a rise timing of the magneto-sensitive body clock SMI for driving the magneto-sensitive body 20 and a rise timing of the sampler clock SMPL for driving the sampler 40.

Further, by observing the displacement of the sampling voltage for a predetermined period after the magneto-sensitive body clock SMI rises, a delay time until the sampling voltage reaches its first peak is detected. Then, the automatic correction circuit 70 sets the rise timings of the magneto-sensitive body clock SMI and the sampler clock SMPL by shifting the rise timings back and forth by a time corresponding to the delay time described above.

The delay synchronization circuit 72 has a plurality of cascaded delay elements 721. The delay synchronization circuit 72 to which the external clock CLK is input outputs a signal having a different amount of delay with respect to the external clock CLK by the plurality of cascaded delay elements 721.

The logic circuit 71 is connected to the detection circuit 60 and the multiplexer 73. Each time the peak sampling state information PS is input from the detection circuit 60, the logic circuit 71 outputs a selection signal Dctrl that selects any one from among the outputs of the plurality of delay elements 721 to the multiplexer 73 to change an output timing of the sampler clock SMPL. The logic circuit 71 monitors the peak sampling state information PS and records the selection signal Dctrl output at the timing at which the induced voltage generated in the coil 30 reaches its peak.

The multiplexer 73 selects any one of the outputs of the delay elements 721 according to the selection signal Dctrl to generate the sampler clock SMPL. The sampler clock SMPL may be a pulse current or a high frequency current.

The clock generation circuit 74 includes a clock$_{gen}$ 741 and a drive circuit 742. The clock$_{gen}$ 741 to which the external clock CLK is input drives the drive circuit 742 to generate the magneto-sensitive body clock SMI synchronized with the external clock CLK. The magneto-sensitive body clock SMI may be a pulse current or a high frequency current. The external clock CLK input to the clock$_{gen}$ 741 is the same as the external clock CLK input to the delay synchronization circuit 72 described above.

(Detection Circuit)

Figure 3:
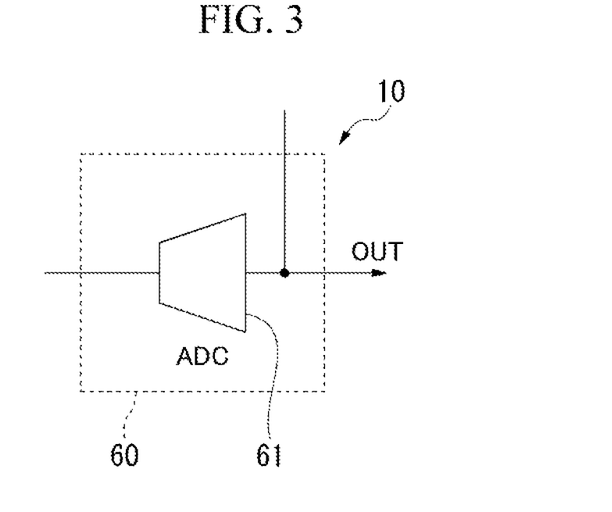
FIG. 3 is a diagram showing details of a detection circuit of the magnetic sensor of FIG. 2.

As shown in FIG. 3, in the magnetic sensor 10 according to the first embodiment of the present invention, the detection circuit 60 includes an analog-to-digital conversion circuit 61 (ADC). The analog-to-digital conversion circuit 61 converts the sampling voltage amplified by the amplifier circuit 50 into peak sampling state information PS.

When a digital output is required for the magnetic sensor 10 during the sensing operation, the above analog-to-digital conversion circuit 61 may be used as a circuit for outputting the digital output signal OUT. Accordingly, there is no need to add a separate circuit as the detection circuit 60, and the detection accuracy can be further improved without increasing the cost of the magnetic sensor 10.

(Magneto-Sensitive Body)

As shown in FIGS. 1 to 3, the magneto-sensitive body 20 is connected to the clock generation circuit 74 of the automatic correction circuit 70. A current flows through the magneto-sensitive body 20 according to the magneto-sensitive body clock SMI generated by the clock generation circuit 74. Accordingly, a magneto-impedance effect (MI effect) is generated in which not only the inductance of the magneto-sensitive body 20 but also the electrical resistance change at the same time.

The magneto-sensitive body 20 changes its electromagnetic properties under the action of an external magnetic field. A magneto-impedance element (MI element) can be used as the magneto-sensitive body 20. The material constituting the magneto-sensitive body 20 is not particularly limited as long as it has soft magnetic properties, but examples thereof include amorphous alloys made of known alloys such as Co—Mn—Si—B and Fe—Si.

(Coil)

As shown in FIGS. 1 to 3, the coil 30 is disposed so that an induced voltage $V_i$ is obtained in proportion to the external magnetic field generated via the magneto-sensitive body 20. The coil 30 is preferably disposed close to (wound around) the magneto-sensitive body 20. This makes it easier to obtain an induced voltage $V_i$ that is proportional to the external magnetic field generated via the magneto-sensitive body 20. A known coil can be used for the coil 30, and it may be configured of a conducting wire, for example.

(Sampler)

As shown in FIGS. 1 to 3, the sampler 40 includes a switch 41 and a capacitor 42 connected in parallel with the coil 30. The sampler 40 samples the induced voltage Vi generated in the coil 30 to obtain a sampling voltage. The switch 41 is driven by the sampler clock SMPL generated by the automatic correction circuit 70. A known switch 41 and capacitor 42 can be used.

(Constant Current Source Circuit)

As shown in FIGS. 1 to 3, the constant current source circuit 80 is connected to the coil 30. The constant current source circuit 80 has a reference voltage circuit 81 (VREF) and a resistor 82. The constant current source circuit 80 operates to provide a constant current for applying a constant DC magnetic field to the magneto-sensitive body 20 during the automatic correction period. In addition, during normal operation, a current proportional to the output signal OUT is caused to flow through the coil 30, and thereby it is reconfigured to realize strong negative feedback.

During automatic correction, a constant strong magnetic field irrelevant to the external magnetic field strength is applied to the magneto-sensitive body 20 by passing a current through the coil 30 to generate a constant magnetic field larger than the external magnetic field. Thereby, it is possible to minimize the influence of the external magnetic field strength. As a result, the sensitivity (amplitude of the induced voltage $V_i$) during automatic correction (during sweeping of the selection signal Dctrl) is maximized, enabling more accurate detection and correction.

Modification Example

Figure 7:
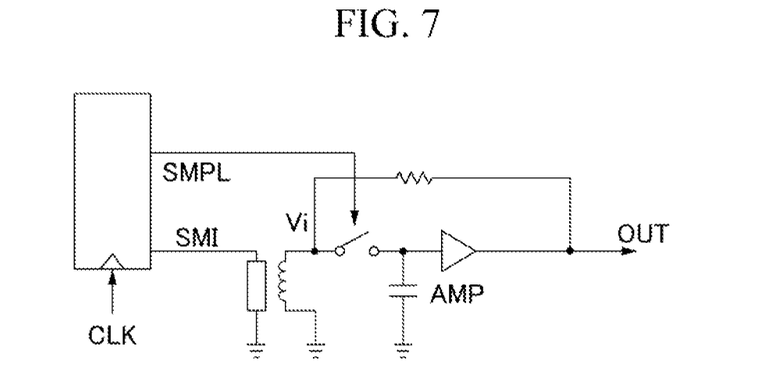
FIG. 7 is a diagram showing a modification example of a magnetic sensor according to an embodiment of the present invention.
Figure 8:
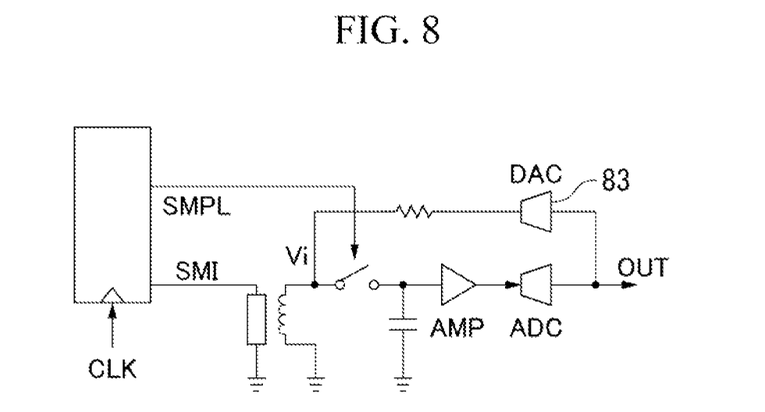
FIG. 8 is a diagram showing another modification example of the magnetic sensor according to the embodiment of the present invention.

As shown in FIGS. 7 and 8, in the magnetic sensor 10 according to the present invention, the constant current source circuit 80 is reconfigured as a strong negative feedback so that the magneto-sensitive body 20, the sampler 40, and the detection circuit 60 may share the resistor 82. As shown in FIG. 8, during normal sensing, when the connection of the reference voltage circuit 81 is switched to the output signal OUT or the output of a digital-to-analog converter (DAC), the magneto-sensitive body 20, the sampler 40, and the detection circuit 60 can share the resistor 82.

Accordingly, the area of the resistive element can be saved, and the cost of the magnetic sensor 10 can be further reduced. The constant current source circuit 80 may be a constant current source. Further, in the constant current source circuit 80, an open loop may be used without using a strong negative feedback (path of resistance).

(Amplifier Circuit)

As shown in FIGS. 1 to 3, the amplifier circuit 50 (AMP) is connected between the sampler 40 and the detection circuit 60. Since the amplifier circuit 50 amplifies the sampling voltage sampled by the sampler 40, it is possible to improve the detection accuracy of the detection circuit 60. Further, during automatic correction, the amplifier circuit 50 may be reused as a preamplifier for the detection circuit 60 by directly connecting the output of the amplifier circuit 50 to the detection circuit 60 in an open loop state where the strong negative feedback configuration of the circuit is cancelled. Thereby, it is possible to further improve the accuracy of the detection circuit 60 without increasing the cost.

(Automatic Correction Method)

An automatic correction method for the magnetic sensor 10 according to the first embodiment of the present invention will be described.

As shown in FIG. 2, during automatic correction, first, a driving current is applied to the magneto-sensitive body 20 by the magneto-sensitive body clock SMI. Accordingly, in the coil 30, an induced voltage $V_i$ proportional to the magnetic field generated by the driving current flowing through the magneto-sensitive body 20 is obtained. At this time, the timing at which the magnitude of the induced voltage Vi generated in the coil 30 is maximized is delayed by Δtopt from the timing at which the magnitude of the magnetic field generated by the current flowing through the magneto-sensitive body 20 is maximized.

The induced voltage $V_i$ is sampled as a sampling voltage by the sampler 40 and input to the detection circuit 60 via the amplifier circuit 50. The analog-to-digital conversion circuit 61 of the detection circuit 60 converts the sampling voltage input via the amplifier circuit 50 into peak sampling state information PS and outputs the information. The peak sampling state information PS and the external clock CLK are input to the automatic correction circuit 70. Then, the automatic correction circuit 70 searches for, determines, and holds the delay amount Δtopt according to the peak sampling state information PS. Then, according to the determined delay amount Δtopt, the magneto-sensitive body clock SMI synchronized with the external clock and the sampler clock SMPL synchronous with the external clock and capable of sampling the peak of the induced voltage Vi generated in the coil 30 by the sampler 40 are generated.

As shown in FIG. 2, when the automatic correction circuit 70 has the above configuration, during automatic correction, the logic circuit 71 sequentially searches the selection signal Dctrl to determine whether or not the sampler 40 has sampled the peak of the induced voltage $V_i$. Then, the logic circuit 71 operates to hold the value of the selection signal Dctrl that selects the optimum output of the delay element 721.

Figure 4:
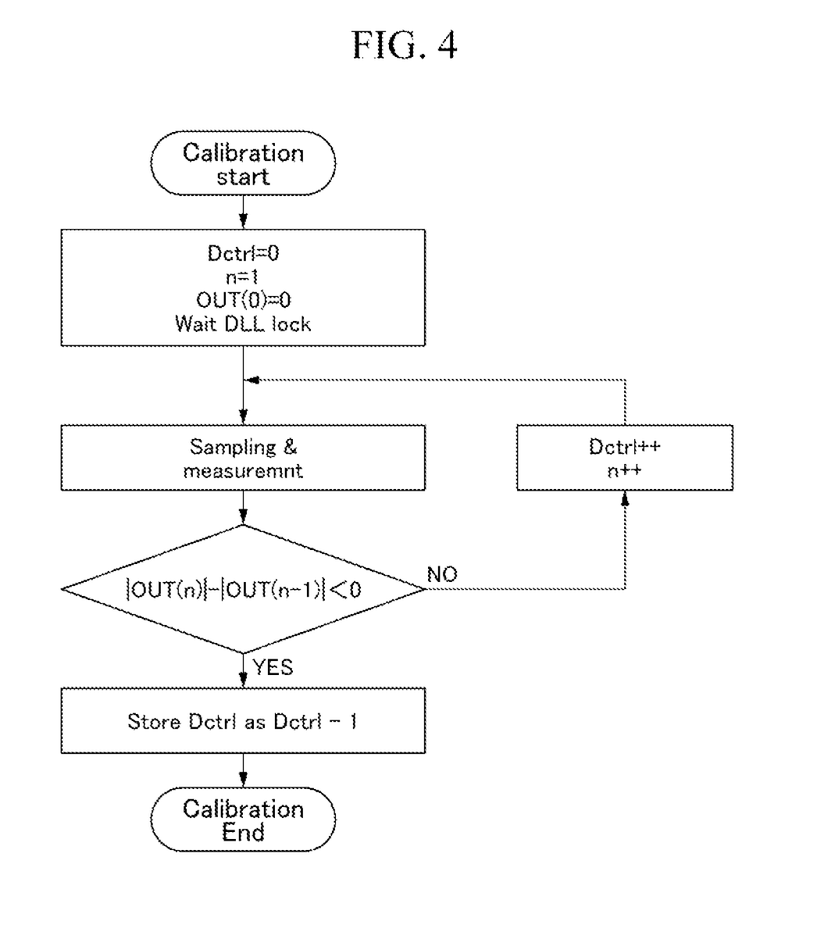
FIG. 4 is a diagram showing a flowchart during automatic correction of the magnetic sensor according to the first embodiment of the present invention.

Specifically, as shown in FIGS. 2 and 4, the logic circuit 71 of the magnetic sensor 10 according to the first embodiment of the present invention starts sweeping the selection signal Dctrl from a value (selection signal $Dctrl_0$) at which the sampler clock SMPL has the minimum delay amount during automatic correction. Here, the minimum delay amount means that the delay amount of a timing ($t_2$) at which the sampler 40 driven by the sampler clock SMPL samples the induced voltage $V_i$ becomes minimum with respect to a rise timing ($t_1$) of the magneto-sensitive body clock SMI. When the magneto-sensitive body clock SMI has a high frequency, $t_1$ is the timing at which the magneto-sensitive body clock SMI first rises and reaches its first peak.

Then, the logic circuit 71 sweeps the delay amount Δtopt of the sampler clock SMPL in synchronization with the external clock CLK by monotonically increasing the selection signal Dctrl sequentially. When an absolute value of the peak sampling state information PS (that is, |output signal OUT|) is equal to or greater than an absolute value of the peak sampling state information PS one clock before each cycle of the external clock CLK, the logic circuit 71 monotonically increases the selection signal Dctrl to continue sweeping the sampling timing. Then, a selection signal $Dctrl_{n-1}$ set one clock before the timing (selection signal $Dctrl_n$) at which the absolute value of the peak sampling state information PS starts to decrease for each cycle of the external clock is held and the sampling timing sweep ends. At this time, the time difference corresponding to the difference between the selection signal $Dctrl_{n-1}$ and a selection signal $Dctrl_0$ is the optimum delay amount Δtopt.

Here, the delay amount Δtopt means a delay amount of a peak timing ($t_3$) of the induced voltage generated in the coil due to the rise of the magneto-sensitive body clock SMI with respect to the rise timing ($t_1$) of the magneto-sensitive body clock SMI.

Accordingly, it is possible to automatically search for the optimum delay amount Δtopt for sampling the peak of the induced voltage Vi generated by the external magnetic field. As a result, it is possible to improve detection accuracy without increasing the cost of the magnetic sensor 10. Further, by using the delay synchronization circuit 72, the delay amount per delay stage of the plurality of delay elements 721 can be fixed with high accuracy regardless of changes in the environment over time. Therefore, it is possible to stably maintain the optimum delay amount Δtopt.

During normal sensing, strong negative feedback control is performed such that the optimum delay amount Δtopt described above is used to generate a sampler clock SMPL that is synchronized with the magneto-sensitive body clock SMI and that allows the sampler 40 to sample the peak of the induced voltage generated in the coil 30. Thereby, it is possible to improve the accuracy of the magnetic sensor 10.

The detection circuit 60 may operate to output the peak sampling state information PS during the automatic correction, to disconnect the connection for sending the peak sampling state information PS, and to obtain the digital output signal OUT from the detection circuit 60 during the sensing operation. Further, when a digital output is required for the magnetic sensor 10 during the sensing operation, the above analog-to-digital conversion circuit 61 may be used as a circuit for outputting the digital output signal OUT. Thereby, there is no need to add a separate circuit as the detection circuit 60, and the detection accuracy can be further improved without increasing the cost of the magnetic sensor 10.

Effect

The resonance frequency of the ringing that occurs across the coil 30 during peak sampling is determined by the product of the coil 30, the parallel capacitance for sampling existing in parallel therewith, and the parasitic capacitance on mounting. Therefore, although the ringing resonance frequency varies from device to device, it is almost uniquely determined at the time of manufacture, and has the characteristic of being almost unaffected by environmental changes such as temperature.

Therefore, with the magnetic sensor 10 according to the first embodiment of the present invention, after the device is manufactured, the delay amount Δtopt between the rise timing of the magneto-sensitive body clock SMI and the peak timing of the induced voltage $V_i$ generated in the coil 30 due to the rise of the magneto-sensitive body clock is determined and stored, and thereby optimum peak sampling can always be performed. As a result, it is possible to prevent deviation of the sampler clock SMPL caused by manufacturing variations, environmental changes, deterioration of the device over time, and the like. Since the delay amount Δtopt is almost unaffected by environmental changes and deterioration of the device over time, manual adjustment can be omitted. Therefore, even when there are environmental changes or manufacturing variations, it is possible to automatically correct the optimum sampling timing for synchronous detection without increasing the cost. Accordingly, the labor for manual correction can be reduced, and the accuracy of the magnetic sensor 10 can be improved.

As described above, with the magnetic sensor 10 according to the first embodiment of the present invention, it is possible to automatically correct the optimum sampling timing for synchronous detection without increasing the cost even when there are environmental changes or manufacturing variations and has excellent detection accuracy.

Second Embodiment

Next, a magnetic sensor 11 and its automatic correction method according to a second embodiment of the present invention will be described with reference to the drawings. In addition, in the case of the same configuration as the above-mentioned embodiment, the same reference numerals may be attached and a description thereof may be omitted.
(Detection Circuit)

Figure 5:
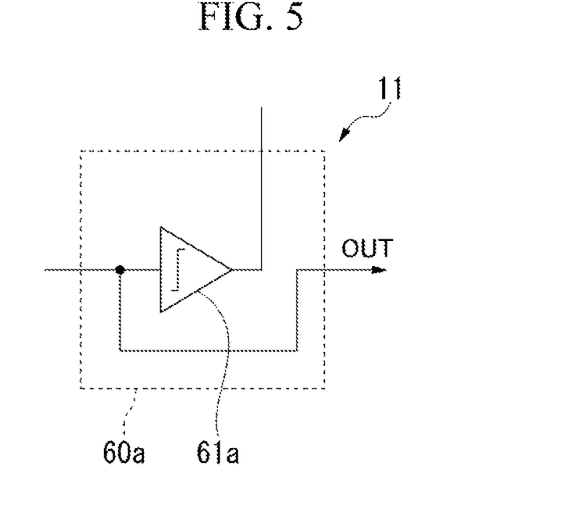
FIG. 5 is a schematic diagram of a magnetic sensor according to a second embodiment of the present invention.

As shown in FIG. 5, in the magnetic sensor 11 according to the second embodiment of the present invention, a detection circuit 60a includes a comparator 61a, and the comparator 61a outputs information binarized according to a predetermined threshold value as peak sampling state information PS. For example, the comparator 61a may use a specific sampling voltage A as a threshold value and output a binarized signal indicating whether the voltage is higher than or lower than the sampling voltage A as the peak sampling state information PS. In the magnetic sensor 11 according to the second embodiment of the present invention, the output signal OUT may be the same as the sampling voltage amplified by the amplifier circuit 50.

As shown in FIG. 5, when the magnetic sensor 11 requires an analog output, it is sufficient that a comparator 61a is added. Accordingly, there is no need to separately provide an analog-to-digital converter as the detection circuit 60a, and it is thus possible to further reduce power consumption and cost.

The configuration of the magnetic sensor 11 according to the second embodiment of the present invention is the same as that of the second embodiment except for the detection circuit 60a.
(Automatic Correction Method)

Figure 6:
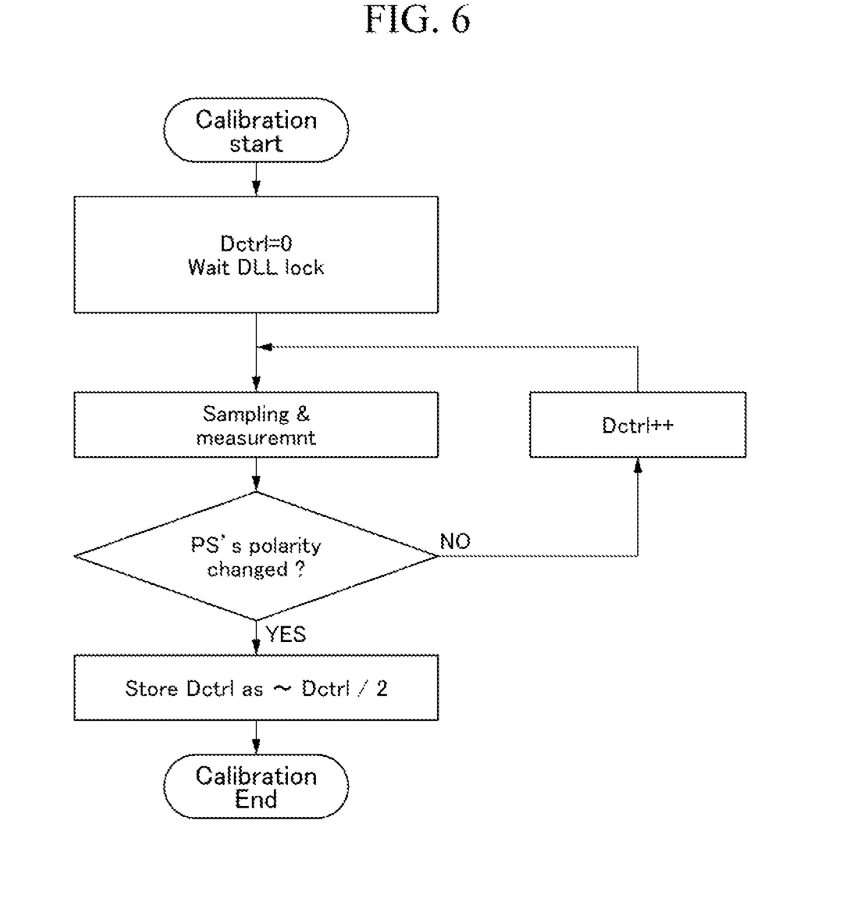
FIG. 6 is a diagram showing a flowchart during automatic correction of the magnetic sensor according to the second embodiment of the present invention.

As shown in FIG. 6, the logic circuit 71 starts sweeping the sampling timing of the selection signal Dctrl from a value at which the sampler clock SMPL has the minimum delay amount during automatic correction. At this time, the comparator 61a sets the sampling voltage sampled by the sampler 40 when the sampler clock SMPL has a value (selection signal $Dctrl_0$) that provides the minimum delay amount as a threshold value. Then, the logic circuit 71 sweeps the sampling timing by synchronizing the delay amount Δtopt of the sampler clock SMPL with the external clock by monotonically increasing the selection signal Dctrl sequentially. The selection signal closest to the timing of ½ of the selection signal $Dctrl_n$ of the timing (selection signal $Dctrl_n$) at which the adjacent binary values of the peak sampling state information PS are inverted (the polarity of the comparator is inverted) for each cycle of the external clock is held as the selection signal Dctrl, and the sampling timing sweep ends. At this time, the difference between the selection signal closest to the timing of ½ of the selection signal $Dctrl_n$ and the selection signal $Dctrl_0$ is the delay amount Δtopt.

Accordingly, it is possible to automatically search for the optimum delay amount Δtopt for sampling the peak of the induced voltage $V_i$. As a result, it is possible to improve detection accuracy without increasing the cost of the magnetic sensor 11. Further, by using the delay synchronization circuit 72, the delay amount per delay stage of the plurality of delay elements 721 can be fixed with high accuracy regardless of changes in the environment over time. Therefore, it is possible to stably maintain the optimum delay amount Δtopt.

During normal sensing, the optimum delay amount Δtopt described above is used to generate a sampler clock SMPL that is synchronized with the magneto-sensitive body clock SMI and that allows the sampler 40 to sample the peak of the induced voltage generated in the coil 30. On the other hand, by connecting the coil 30 so that a current proportional to the output signal OUT flows through the coil 30 as shown in FIG. 7, it is possible to realize strong negative feedback while maintaining the maximum loop gain. Thereby, it is possible to further improve the accuracy of the magnetic sensor 11.

"Biomagnetic Measurement Device"

A biomagnetic measurement device according to an embodiment of the present invention will be described.

Figure 9:
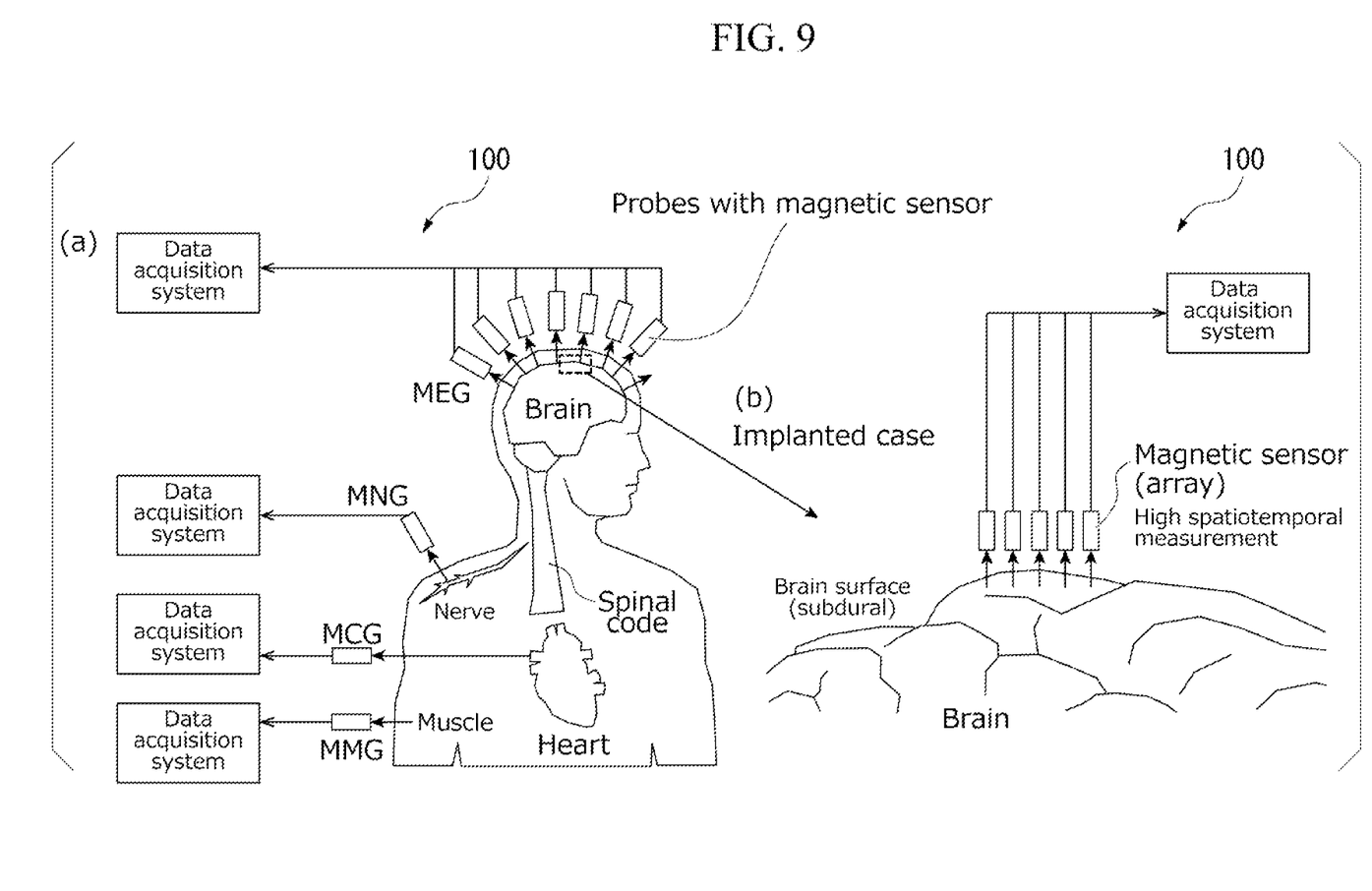
FIG. 9 is a schematic diagram of a biomagnetic measurement device according to an embodiment of the present invention.

As shown in FIG. 9, a biomagnetic measurement device 100 according to an embodiment of the present invention includes the magnetic sensor described in the above embodiments and a biomagnetic measurement unit that measures magnetism emitted by a living body using an output signal from the magnetic sensor. The biomagnetic measurement device 100 according to the embodiment of the present invention may include the above-mentioned N (channels) of magnetic sensors, a control device, and a signal processing device. Biomagnetic field measurements such as magnetoencephalography, magnetocardiography, and magnetomyography can be performed through N-channel simultaneous measurement by the control device and subsequent processing in the signal processing device. The biomagnetic measurement device 100 may have a configuration in which a probe (array) including a magnetic sensor and a data acquisition system are paired. In addition, the connection between the probe and the data acquisition system may be wired, wireless, and combinations thereof.

This enables the realization of high-resolution (picotesla level) biomagnetic measurement devices that can operate stably, in a compact size and with low power consumption. Therefore, there is no need to use a magnetic sensor head (such as SQUID) for biomagnetic measurement in the related art, and significant downsizing and cost reduction can be achieved.

Examples of the biomagnetic measurement device 100 include, but are not particularly limited to, magnetoencephalography (MEG), magnetoneurography (MNG), magnetocardiography (MCG), magnetomyography (MMG), and bio-embedded brain activity measurement.

Throughout the specification, when a part is referred to as "having" or "including" a component, this does not exclude other components, unless specifically stated to the contrary, and means that other components may be further included.

In addition, the term " . . . unit" described in the specification means a unit that processes at least one function or operation, which may be implemented as hardware or software, or may be implemented in a combination of hardware and software.

In addition, it is possible to appropriately replace the components in the above-described embodiments with well-known components without departing from the gist of the present invention, and the modification examples described above may be combined as appropriate.

INDUSTRIAL APPLICABILITY

From the above, according to the present invention, it is possible to provide a magnetic sensor and a biomagnetic measurement device capable of automatically correcting the optimum sampling timing for synchronous detection at low cost even when there are environmental changes or manufacturing variations, and thus have high industrial applicability.

REFERENCE SIGNS LIST

11: Magnetic sensor
20 Magneto-sensitive body
30: Coil
40 Sampler
41: Switch
42: Capacitor
50 Amplifier circuit
60, 60a: Detection circuit
61: Analog-to-digital conversion circuit
61a: Comparator
70 Automatic correction circuit
71: Logic circuit
72: Delay synchronization circuit
721: Delay element
73: Multiplexer
74: Clock generation circuit
741: Clock gen
742: Drive circuit
80 Constant current source circuit
81: Reference voltage circuit
82: Resistor
83: Digital-to-analog conversion circuit
100: Biomagnetic measurement device

What is claimed is:

1. A magnetic sensor comprising:
a magneto-sensitive body whose electromagnetic properties change under an action of an external magnetic field;
a coil disposed to obtain an induced voltage proportional to the external magnetic field;
a sampler configured to sample the induced voltage generated in the coil and obtain a sampling voltage; and
an automatic correction circuit configured to relatively adjust a rise timing of a magneto-sensitive body clock for driving the magneto-sensitive body and a rise timing of a sampler clock for driving the sampler according to the sampling voltage, wherein
the automatic correction circuit detects a delay time until the sampling voltage reaches its first peak by observing displacement of the sampling voltage for a predetermined period after the magneto-sensitive body clock rises, and sets the rise timings of the magneto-sensitive body clock and the sampler clock by shifting the rise timings back and forth by a time corresponding to the delay time.

2. The magnetic sensor according to claim 1, wherein the automatic correction circuit includes
a delay synchronization circuit having a plurality of cascaded delay elements,
a logic circuit that outputs a selection signal Dctrl that selects any one from among outputs of the plurality of delay elements in the delay synchronization circuit each time the sampling voltage is input, and records the selection signal Dctrl output at a timing at which the induced voltage generated in the coil reaches a peak,
a multiplexer that selects any one of the outputs of the plurality of delay elements in the delay synchronization circuit according to the selection signal Dctrl to generate the sampler clock, and
a clock generation circuit that generates the magneto-sensitive body clock.

3. The magnetic sensor according to claim 1, further comprising a detection circuit configured to output peak sampling state information having information on a timing at which the induced voltage generated in the coil reaches a peak, according to the sampling voltage.

4. The magnetic sensor according to claim 3, wherein
the detection circuit includes an analog-to-digital conversion circuit, and
the analog-to-digital conversion circuit converts the sampling voltage into the peak sampling state information.

5. The magnetic sensor according to claim 3, wherein
the detection circuit includes a comparator, and
the comparator outputs information binarized according to a predetermined threshold value as the peak sampling state information.

6. The magnetic sensor according to claim 1, wherein a constant current source circuit is connected to the coil.

7. A biomagnetic measurement device comprising:
the magnetic sensor according to claim 1; and
a biomagnetic measurement unit configured to measure magnetism emitted by a living body using an output signal from the magnetic sensor.

* * * * *